United States Patent
Kim et al.

(10) Patent No.: US 10,626,247 B2
(45) Date of Patent: Apr. 21, 2020

(54) PLASTICIZER COMPOSITION, RESIN COMPOSITION, AND PREPARATION METHODS THEREFOR

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 86 days.

(21) Appl. No.: 15/572,735

(22) PCT Filed: Nov. 25, 2016

(86) PCT No.: PCT/KR2016/013726
§ 371 (c)(1),
(2) Date: Nov. 8, 2017

(87) PCT Pub. No.: WO2017/091040
PCT Pub. Date: Jun. 1, 2017

(65) Prior Publication Data
US 2018/0142078 A1     May 24, 2018

(30) Foreign Application Priority Data
Nov. 27, 2015   (KR) .................. 10-2015-0167862

(51) Int. Cl.
| | |
|---|---|
| *C08K 5/10* | (2006.01) |
| *C08K 5/00* | (2006.01) |
| *C08K 5/12* | (2006.01) |
| *C08K 5/11* | (2006.01) |
| *C08K 13/00* | (2006.01) |
| *C07C 59/265* | (2006.01) |
| *C07C 69/80* | (2006.01) |
| *C08L 101/00* | (2006.01) |

(52) U.S. Cl.
CPC .......... *C08K 5/0016* (2013.01); *C07C 59/265* (2013.01); *C07C 69/80* (2013.01); *C08K 5/11* (2013.01); *C08K 5/12* (2013.01); *C08K 13/00* (2013.01); *C08L 101/00* (2013.01); *C08K 2201/014* (2013.01)

(58) Field of Classification Search
CPC .................................................. C08K 5/0016
See application file for complete search history.

(56) References Cited

U.S. PATENT DOCUMENTS

| | | |
|---|---|---|
| 2003/0015279 A1 | 1/2003 | Kusek |
| 2004/0001941 A1 | 1/2004 | Kusek |
| 2005/0049341 A1 | 3/2005 | Grass et al. |
| 2006/0127607 A1* | 6/2006 | Okubo .................... C07C 69/82 428/1.3 |
| 2007/0006961 A1 | 1/2007 | Kusek |
| 2007/0037926 A1 | 2/2007 | Olsen et al. |
| 2008/0088060 A1* | 4/2008 | Ito .............................. C08J 5/18 264/291 |
| 2008/0318042 A1 | 12/2008 | Kusek |
| 2010/0113664 A1 | 5/2010 | Bradshaw et al. |
| 2010/0316861 A1* | 12/2010 | Kubler ....................... C08J 5/18 428/220 |
| 2011/0021680 A1 | 1/2011 | Colle et al. |
| 2013/0137789 A1* | 5/2013 | Olsen ....................... C08K 5/12 521/145 |
| 2013/0317152 A1 | 11/2013 | Becker et al. |
| 2014/0228494 A1 | 8/2014 | Colle et al. |

FOREIGN PATENT DOCUMENTS

| | | |
|---|---|---|
| CN | 1056507 A | 11/1991 |
| CN | 101967098 A | 2/2011 |
| CN | 104292600 A | 1/2015 |
| KR | 1020050016207 A | 2/2005 |
| KR | 1020080055800 A | 6/2008 |
| KR | 1020090074177 A | 7/2009 |
| KR | 1020140005908 A | 1/2014 |
| KR | 1020150131811 A | 11/2015 |
| WO | 2007/021987 A1 | 2/2007 |
| WO | 2009118261 A1 | 10/2009 |
| WO | 2011071674 A1 | 6/2011 |

OTHER PUBLICATIONS

"Review in Applied Performances of a New Plasticizer DPHP", Guo Hao-ran, Zhu Li-qin (Beijing Research Institute of Chemical Industry, SINOPEC, Beijing, 100013), Dec. 20, 2006; pp. 36-39.

* cited by examiner

*Primary Examiner* — Michael F Pepitone
(74) *Attorney, Agent, or Firm* — Denton US LLP

(57) ABSTRACT

The present invention relates to a plasticizer composition, a resin composition, and preparation methods therefor, and can provide: a plasticizer capable of improving physical properties such as plasticizing efficiency, migration, tensile strength, elongation, stress migration and light resistance, which are required in sheet formulation, when used as a plasticizer of a resin composition by improving inferior physical properties generated because of structural limitations; and a resin composition containing the same.

17 Claims, 2 Drawing Sheets

[Figure 1]
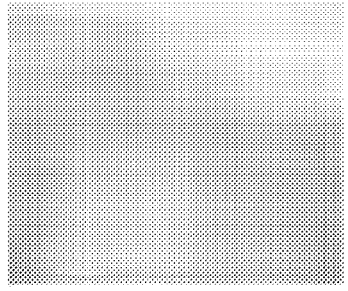
EXAMPLE 6
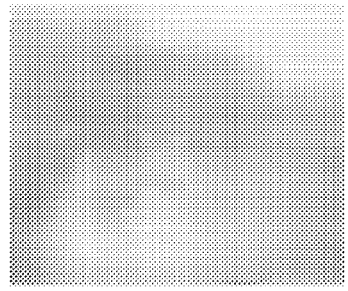
EXAMPLE 1
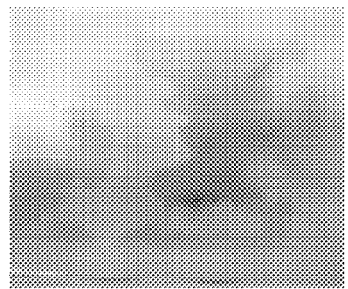
COMPARATIVE EXAMPLE 1
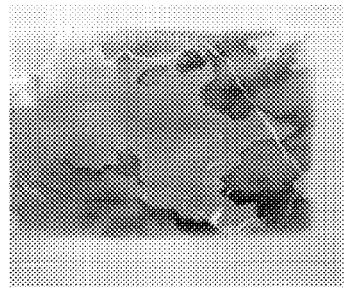
COMPARATIVE EXAMPLE 3

[Figure 2]
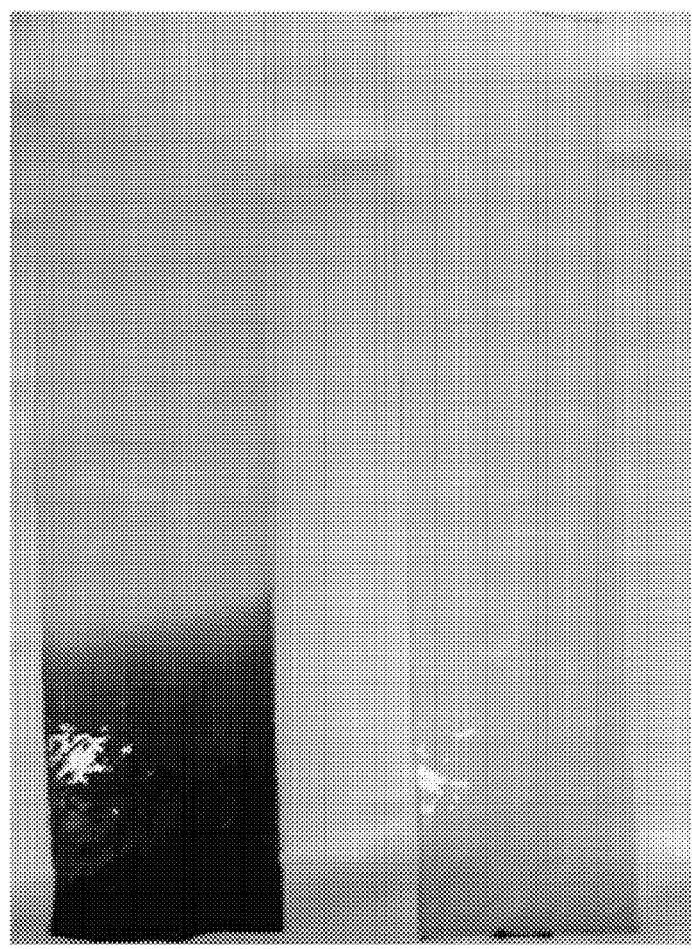

PLASTICIZER COMPOSITION, RESIN COMPOSITION, AND PREPARATION METHODS THEREFOR

CROSS-REFERENCE TO RELATED APPLICATION

This application is a National Stage Application of International Application No. PCT/KR2016/013726, filed Nov. 25, 2016, and claims the benefit of Korean Patent Application No. 10-2015-0167862, filed on Nov. 27, 2015, contents of which are incorporated herein by reference in their entirety for all purposes as if fully set forth below.

TECHNICAL FIELD

Technical Field

The present invention relates to a plasticizer composition, a resin composition, and preparation methods therefor.

Background Art

Generally, a plasticizer forms an ester corresponding to the plasticizer through a reaction between an alcohol and a polycarboxylic acid such as phthalic acid or adipic acid. Also, there has been continuing research on compositions of plasticizers that can replace phthalate-based plasticizers such as terephthalate-based, adipate-based, and other polymer-based plasticizers in consideration of domestic and international regulations on phthalate-based plasticizers which are harmful to human bodies.

Meanwhile, among phthalate-based products, dipropylheptyl phthalate (DPHP) is a product which is not affected by environmental regulations. Most phthalate products having a molecular weight lower than DPHP, which include most conventional phthalates, particularly diisononyl phthalate, are affected by the environmental regulations. However, no regulations have been imposed on dipropylheptyl phthalate (DPHP) so far, DPHP has been continuously used in industries which have no regulations or are expected to have no regulations, and it is required for qualities of DPHP to be improved to resolve complaints about the qualities when used.

In compound industries requiring heat resistance and cold resistance as main desired physical properties, suitable plasticizers should be generally used in consideration of the desired physical properties. In the case of PVC compounds used for calendaring sheets or electric wires and tubes for automobiles, additives such as a plasticizer, a stabilizer, and a filler are mixed with a PVC resin depending on characteristics required for corresponding specifications, such as tensile strength, elongation rate, plasticizing efficiency, volatile loss, cold resistance, etc. In this case, amounts of the mixed additives may also vary to secure the desired physical properties.

Because the use of diisononyl phthalate (DINP), which is typically used as a compound in calendaring sheets, electric wires for automobiles, and the like, is currently being regulated due to environmental issues, there is an increasing demand for development of environmentally friendly products to replace DINP. Therefore, it is necessary to develop novel products having an equivalent or higher level of quality to replace DINP.

Prior-Art Document

Patent Document

Korean Unexamined Patent Publication No. 10-2009-0074177

DISCLOSURE

Technical Problem

Accordingly, the present inventors have continued to conduct research on plasticizers and found a plasticizer composition capable of remarkably improving physical properties of a PVC resin composition. Therefore, the present invention has been completed on the basis of these facts.

That is, it is an object of the present invention to provide a plasticizer capable of improving physical properties such as plasticizing efficiency, migration, a gelling property, and the like, which are required in sheet formulations and the like, when used as a plasticizer of a resin composition, a preparation method therefor, and a resin composition including the plasticizer.

Technical Solution

To solve the above problems, according to one aspect of the present invention, there is provided a plasticizer composition which includes di(2-propylheptyl) phthalate; and a citrate-based material, wherein the di(2-propylheptyl) phthalate and the citrate-based material are included at a weight ratio of 99:1 to 1:99.

The di(2-propylheptyl) phthalate and the citrate-based material may be included at a weight ratio of 95:5 to 50:50.

The di(2-propylheptyl) phthalate and the citrate-based material may be included at a weight ratio of 95:5 to 60:40.

The citrate-based material may be one single compound or a mixture of two or more types selected from hybrid alkyl-substituted citrates having 4 to 9 carbon atoms and non-hybrid alkyl-substituted citrates having 4 to 9 carbon atoms, and the alkyl is linear or branched, and the alkyl may be linear or branched.

The citrate-based material may be one single compound or a mixture of two or more types selected from hybrid alkyl-substituted citrates having 4 to 9 carbon atoms, and the alkyl may be linear or branched.

The citrate-based material may be one single compound or a mixture of two or more types selected from non-hybrid alkyl-substituted citrates having 4 to 9 carbon atoms, and the alkyl may be linear or branched.

The plasticizer composition may further include an additive, and the additive may include one or more selected from the group consisting of a filler, a stabilizer, a processing aid, a lubricant, a dispersant, a foaming agent, a viscosity depressant, and titanium dioxide.

The plasticizer composition may further include an epoxidized ester.

The epoxidized ester may be an epoxidized oil, an epoxidized alkyl monoester, or a mixture thereof. In this case, the epoxidized oil may include one or more selected from the group consisting of epoxidized soybean oil, epoxidized castor oil, epoxidized linseed oil, epoxidized palm oil, and epoxidized tall oil, and the epoxidized alkyl monoester may include one or more selected from the group consisting of an epoxidized alkyl stearate, an epoxidized alkyl oleate, an epoxidized alkyl linoleate, and a mixture thereof, all of which contain a linear or branched alkyl group having 1 to 10 carbon atoms as an alkyl group. The epoxidized ester may be added at a content of 1 to 50 parts by weight based on 100 parts by weight of the sum of weights of the phthalate-based material and the citrate-based material.

To solve the above problems, according to another aspect of the present invention, there is provided a method for preparing a plasticizer composition, which includes preparing di(2-propylheptyl) phthalate and a citrate-based material; and blending the di(2-propylheptyl) phthalate and the citrate-based material at a weight ratio of 99:1 to 1:99 to obtain a plasticizer composition, wherein the citrate-based material is a single compound or a mixture.

When the citrate-based material is a single compound, the citrate-based material may be prepared through a direct esterification reaction in which citric acid reacts with one alcohol selected from primary alcohols having 4 to 9 carbon atoms.

When the citrate-based material is a mixture, a terephthalate compound may be prepared through a direct esterification reaction in which citric acid reacts with one alcohol selected from primary alcohols having 4 to 9 carbon atoms; or a trans-esterification reaction in which one alcohol selected from primary alcohols having 4 to 9 carbon atoms reacts with one citrate selected from non-hybrid alkyl-substituted citrates having 4 to 9 carbon atoms.

The preparation method may further include adding an epoxidized ester after the blending.

To solve the above problems, according to still another aspect of the present invention, there is provided a resin composition which includes 100 parts by weight of a resin; and 5 to 150 parts by weight of the aforementioned plasticizer composition.

The resin may include one or more selected from the group consisting of ethylene vinyl acetate, polyethylene, polypropylene, polyvinyl chloride, polystyrene, polyurethane, and a thermoplastic elastomer.

The resin composition may include one or more materials selected from the group consisting of an electric wire, a flooring material, an automotive interior material, a film, a sheet, wallpaper, and a tube.

Advantageous Effects

The plasticizer composition according to one exemplary embodiment of the present invention can provide excellent physical properties such as an absorption rate and resistance to volatility as well as excellent plasticizing efficiency, tensile strength, and elongation rate when used in a resin composition.

DESCRIPTION OF DRAWINGS

FIG. 1 is an image showing results obtained by evaluating light resistance of specimens prepared in Examples and Comparative Examples.

FIG. 2 is an image showing results obtained by evaluating heat resistance of specimens prepared in Examples.

BEST MODE

Examples

Hereinafter, the present invention will be described in detail with reference to embodiments thereof to describe the present invention more clearly. However, it should be understood that the embodiments of the present invention can be implemented in various forms and are not intended to limit the scope of the present invention. The embodiments of the present invention are provided herein to describe the present invention more fully to people having ordinary skill in the art.

Preparative Example 1: Preparation of DPHP 498.0 g of purified phthalic acid (PA), 1,170 g of 2-propylheptyl alcohol (2-PH) (a 1.0:3.0 molar ratio of PA to 2-PH), and 1.54 g (0.31 parts by weight based on 100 parts by weight of the PA) of a titanium-based catalyst (tetraisopropyl titanate (TIPT)) serving as a catalyst were added to a 3 L 4-neck reactor equipped with a cooler, a condenser, a decanter, a reflux pump, a temperature controller, an agitator, and the like and slowly heated to approximately 170° C. Produced water started to be generated in the vicinity of approximately 170° C., and an esterification reaction was performed for approximately 4.5 hours while continuously adding nitrogen gas at a reaction temperature of approximately 220° C. under an atmospheric pressure condition. When an acid value thereof reached 0.01, the reaction was terminated.

After the reaction was terminated, distillation extraction was performed for 0.5 to 4 hours under reduced pressure to remove unreacted raw materials. To remove the unreacted raw materials so that the amount of the unreacted raw materials was lower than a predetermined content, steam extraction was performed for 0.5 to 3 hours at reduced pressure using steam. The reaction solution was cooled to a temperature of approximately 90° C., and then neutralized with an alkaline solution. In addition, the reaction solution was also able to be washed, and then dehydrated to remove moisture. A filter medium was added to the moisture-free reaction solution, stirred for a predetermined time, and then filtered to finally obtain 1,326.7 g of di(2-propylheptyl) phthalate (yield: 99.0%).

Preparative Example 2: Preparation of TBC 384 g of citric acid and 580 g of butanol were used as reaction raw materials to finally obtain 706 g of tributyl citrate (yield: 98%).

Preparative Example 3: Preparation of TOC 384 g of citric acid and 1,014 g of 2-ethylhexanol were used as reaction raw materials to finally obtain 1,029 g of tri-2-ethylhexyl citrate (yield: 98%).

Preparative Example 4: Preparation of BOC 1,000 g of TOC prepared in Preparative Example 6 and 150 g of n-butanol were used as reaction raw materials to perform a trans-esterification reaction, thereby finally obtaining 940 g of butyloctyl citrate. For reference, The product is composition and includes main components, which were distinguished by alkyl group(s) is bound to three ester groups of the citrate compound: BOC in which two butyl groups are bound to the three ester groups, BOC in which one butyl group is bound to the three ester groups, and TOC in which no butyl group is bound to the three ester groups. In this case, each of them was present at weight ratios of approximately 10%, 40%, and 50%, respectively.

Examples and Comparative Examples were configured using the aforementioned compounds prepared in Preparative Examples as follows. The configurations are listed in the following Table 1.

TABLE 1

|  | Phthalate | Citrate | Mixing ratio |
|---|---|---|---|
| Example 1 | DPHP | TBC | 7:3 |
| Example 2 | DPHP | TBC | 3:7 |
| Example 3 | DPHP | TOC | 7:3 |
| Example 4 | DPHP | TOC | 3:7 |
| Example 5 | DPHP | BOC | 5:5 |
| Comparative Example 1 | DPHP | — |  |
| Comparative Example 2 | — | TBC |  |
| Comparative Example 3 | DINP | — |  |
| Comparative Example 4 | DIDP | — |  |
| Comparative Example 5 | DEHP | TBC |  |

<Test Items>

Measurement of Hardness

Shore A hardness at 25° C., 3 T 10 s was measured using ASTM D2240.

Measurement of Tensile Strength

Through an ASTM D638 method, a specimen was drawn at a cross head speed of 200 mm/min (1 T) using a test apparatus, U.T.M (Manufacturer: Instron, Model name: 4466), and a point at which the specimen was broken was then measured. The tensile strength was calculated as follows.

Tensile strength (kgf/mm$^2$)=Load value (kgf)/Thickness (mm)×Width (mm)

Measurement of Elongation Rate

Through an ASTM D638 method, a specimen was drawn at a cross head speed of 200 mm/min (1 T) using the U.T.M, and a point at which the specimen was broken was then measured. The elongation rate was calculated as follows.

Elongation rate (%)=[Length after elongation/Initial length]×100

Measurement of Migration Loss

A specimen having a thickness of 2 mm or more was obtained according to KSM-3156, PS plates were attached to both sides of the specimen, and a load of 2 kgf/cm$^2$ was then applied thereto. The specimen was placed in a forced convection oven (80° C.) for 72 hours, taken out, and then cooled at room temperature for 4 hours. Thereafter, the PS plates attached to both sides of the specimen were removed, and weights of the specimens were measured before and after the specimens were placed in the oven. Then, a migration loss was calculated through the following equation.

Migration loss (%)=[(Initial weight of specimen at room temperature−Weight of specimen after being in oven)/Initial weight of specimen at room temperature]×100

Measurement of Volatile Loss

The specimen thus prepared was processed at 100° C. for 72 hours, and a weight of the specimen was measured.

Volatile loss (%)=[(Initial weight of specimen−Weight of specimen after processing)/Initial weight of specimen]×100

Stress Test

A stress test was carried out by keeping the specimen in a bent state at room temperature for a predetermined time, and then observing a degree of migration (a leaking degree) that was then indicated by numerical values. In this case, it is revealed that the nearer a numerical value is to 0, the better the characteristics of the specimen were.

Measurement of Light Resistance

Through an ASTM 4329-13 method, the specimen was held on QUV and irradiated with UV rays for 400 hours. Thereafter, changes in state and color of the specimen were observed.

Measurement of Heat Resistance

A specimen having a thickness of 0.5 T was thermally treated at a temperature of 220° C. and a rate of 25 mm/3 min in a Mathis oven to observe heat-resistant characteristics of the specimen.

Cold Resistance

Five specimens thus prepared were kept at a certain temperature for 3 minutes, and then struck to measure a temperature at which 3 of the five specimens were broken.

Experimental Example 1: Evaluation of Physical Properties of Resin Specimens

Specimens were manufactured using the mixed plasticizer compositions of Examples and Comparative Examples listed in Table 1.

The specimens were manufactured as follows with reference to ASTM D638. 40 parts by weight of each of the plasticizer compositions prepared in Examples and Comparative Examples, 5 parts by weight of RUP144 as a stabilizer, and 30 parts by weight of OMYA 1 T as a filler were mixed with respect to 100 parts by weight of a polyvinyl chloride (PVC) resin (LS100) and mixed at 700 rpm and 98° C. The resulting mixture was processed at 160° C. for 4 minutes in a roll mill, and processed at 180° C. for 2.5 minutes (at a low pressure) and 2 minutes (at a high pressure) using a press to manufacture specimens.

The aforementioned tests were performed on the specimens to evaluate each of the test items. The results are listed in the following Table 2.

TABLE 2

|  | Hardness (Shore A) | Tensile Strength (kg/cm$^2$) | Elongation Rate (%) | Migration Loss (%) | Volatile Loss (%) | Cold Resistance (° c.) | Absorption Rate (sec) | Stress Test (7 days) |
|---|---|---|---|---|---|---|---|---|
| Example 1 | 89.7 | 197.7 | 239.1 | 1.21 | 2.90 | −32 | 320 | 0.5 |
| Example 2 | 82.6 | 171.2 | 245.9 | 1.56 | 6.74 | −48 | 247 | 0 |
| Example 3 | 90.9 | 191.1 | 252.6 | 1.30 | 0.72 | −30 | 452 | 0.5 |
| Example 4 | 91.7 | 202.4 | 251.7 | 0.32 | 0.36 | −28 | 492 | 1.0 |
| Example 5 | 90.8 | 188.7 | 251.2 | 1.51 | 0.68 | −31 | 330 | 1.0 |
| Comparative Example 1 | 92.3 | 182.3 | 232.0 | 1.75 | 2.14 | −24 | 481 | 1.0 |
| Comparative Example 2 | 78.5 | 154.6 | 189.7 | 4.50 | 15.60 | −35 | 187 | 1.5 |
| Comparative Example 3 | 90.0 | 185.6 | 232.2 | 1.34 | 1.90 | −29 | 388 | 1.0 |
| Comparative Example 4 | 91.5 | 185.7 | 230.5 | 1.05 | 0.80 | −26 | 450 | 0 |

TABLE 2-continued

|  | Hardness (Shore A) | Tensile Strength (kg/cm$^2$) | Elongation Rate (%) | Migration Loss (%) | Volatile Loss (%) | Cold Resistance (° c.) | Absorption Rate (sec) | Stress Test (7 days) |
|---|---|---|---|---|---|---|---|---|
| Comparative Example 5 | 82.6 | 165.8 | 191.4 | 3.51 | 11.23 | −35 | 240 | 1.0 |

Referring to Table 2, it can be seen that processability was rather deteriorated due to a very rapid absorption rate, mechanical properties were not satisfied at a desired level due to very poor levels of tensile strength and elongation rate, and migration or volatile loss were severely degraded in the case of the specimen of Comparative Example 2 in which only the citrate-based material was used without being mixed with phthalate when compared to the specimens of Examples, and also that resistance to stress was severely deteriorated. Therefore, it can be seen that it was difficult to apply the specimen of Comparative Example 2 to products. Also, it can be seen that the specimen of Comparative Example 1 in which the citrate-based material was not mixed has inferior mechanical properties and poor cold-resistant characteristics, compared to the specimens of Examples in which the citrate-based material was mixed, which made it difficult to apply the specimen in a low-temperature environment.

Referring to Examples 1 to 5, it can be seen that all the specimens of Examples 1 to 5 had physical properties equal to or superior to the physical properties of the specimens of Comparative Examples 3 and 4 in which a phthalate product which had excellent physical properties but was difficult to use due to environmental problems was used as a product used in a prior art.

Also, it can be seen that volatile loss characteristics were inferior and mechanical properties were also not improved to a desired level even when DEHP on which the strictest environmental regulations have been imposed was used in the case of the specimen of Comparative Example 5.

Based on these results, it can be seen that mechanical properties and processability characteristics were able to be secured due to suitable levels of hardness and absorption rate when DPHP and the citrate-based material were mixed and used as in Examples, and the specimens had resistance to temperature change by properly adjusting the ratio of the DPHP and the citrate-based material to control the characteristics such as volatile loss, cold resistance, and the like.

listed in the following Table 3. Specimens were manufactured from these configurations in the same manner as in Experimental Example 1.

TABLE 3

|  | Phthalate | Citrate | Mixing Ratio | Additional Material | Input |
|---|---|---|---|---|---|
| Example 1 | DPHP | TBC | 7:3 |  |  |
| Example 2 | DPHP | TBC | 3:7 |  |  |
| Example 3 | DPHP | TOC | 7:3 |  |  |
| Example 4 | DPHP | TOC | 3:7 |  |  |
| Example 5 | DPHP | BOC | 5:5 |  |  |
| Example 6 | DPHP | TBC | 7:3 | ESO | Approximately 10 parts by weight |
| Example 7 | DPHP | TOC | 7:3 | ESO | Approximately 25 parts by weight |
| Example 8 | DPHP | BOC | 5:5 | ESO | Approximately 50 parts by weight |
| Example 9 | DPHP | TOC | 7:3 | eFAEHE | Approximately 25 parts by weight |
| Example 10 | DPHP | BOC | 5:5 | eFABE | Approximately 50 parts by weight |
| Reference Example 1 | DPHP | BOC | 5:5 | ESO | Approximately 70 parts by weight |

*ESO: epoxidized soybean oil
*eFAEHE: epoxidized fatty acid 2-ethylhexyl ester
*eFABE: epoxidized fatty acid butyl ester The aforementioned tests were performed on the specimens to evaluate each of the test items. The results are listed in the following Table 4.

TABLE 4

|  | Hardness (Shore A) | Tensile Strength (kg/cm2) | Elongation Rate (%) | Migration Loss (%) | Volatile Loss (%) | Cold Resistance (° C.) | Absorption Rate (sce) | Stress Test (7 days) |
|---|---|---|---|---|---|---|---|---|
| Example 6 | 90.0 | 205.3 | 234.1 | 0.87 | 1.62 | −30 | 310 | 0 |
| Example 7 | 90.3 | 209.7 | 261.8 | 0.25 | 0.12 | −26 | 412 | 0 |
| Example 8 | 91.0 | 207.2 | 258.7 | 0.78 | 0.32 | −28 | 315 | 0.5 |
| Example 9 | 88.4 | 201.4 | 256.7 | 1.77 | 0.75 | −32 | 411 | 0 |
| Example 10 | 87.0 | 193.5 | 287.4 | 1.60 | 0.47 | −30 | 284 | 1.0 |
| Reference Example 1 | 93.8 | 198.5 | 218.9 | 0.73 | 0.30 | −20 | 345 | 2.0 |

Experimental Example 2: Evaluation of Physical Properties of Resin Specimens

To check a change in effect when an epoxidized ester was additionally added, additional examples were configured as Plasticizers in which an epoxidized oil or an epoxidized alkyl monoester was used as the epoxidized ester material were used as additional configurations in Examples 6 to 10. Referring to Table 4, it can be seen that the mechanical properties and the physical properties such as volatile loss or migration loss were further improved and hardness and cold resistance were not severely degraded when the epoxidized ester was additionally added in the case of the specimen of Example 6, in which ESO was additionally added to the existing specimen of Example 1, or Example 7, in which ESO was additionally added to the existing specimen of Example 3, and also that resistance to stress was improved.

Further, when the epoxidized ester was added, it was necessary to adjust a content of the epoxidized ester. In this case, referring to Reference Example 1, it can be seen that the resistance to stress might be degraded when the epoxidized ester was added at a content of 50 parts by weight or more.

Also, FIG. 1 shows the results of the light resistance test performed on the specimens of Examples 1 and 6 and Comparative Examples 1 and 3. In this case, it can be seen that degrees of discoloration of the specimens of Comparative Examples were severe enough to be recognizable with the naked eye, compared to the specimens of Examples. Therefore, it can be seen that light-resistant characteristics were able to be improved by additionally adding the epoxidized ester.

Referring to FIG. 2, it can be seen that a degree of combustion of the specimen of Example 9 in which the epoxidized ester was additionally added was significantly low when heat was applied to the specimen, compared to the specimen of Example 3 in which the epoxidized ester was not added. Therefore, it can be seen that heat resistance was able to be improved by adding the epoxidized ester.

Although preferred embodiments of the present invention have been shown and described in detail, it should be appreciated by those skilled in the art that various modifications and changes may be made in these embodiments without departing from the principles and spirit of the present invention, the scope of which is defined in the claims and their equivalents.

MODE FOR INVENTION

Hereinafter, the present invention will be described in detail.

First, the present invention has a technical feature in that a plasticizer composition capable of improving inferior physical properties caused due to structural limitations is provided.

According to one exemplary embodiment of the present invention, there is a provided a plasticizer composition including di(2-propylheptyl) phthalate. Specifically, the di(2-propylheptyl) phthalate may be used at a content in a range of 1 to 99% by weight, 20 to 99% by weight, 40 to 99% by weight, 50 to 95% by weight, or 60 to 90% by weight based on the total weight of the composition.

The di(2-propylheptyl) phthalate is not a material which infringes environmental issues like phthalate-based plasticizers such as diisodecyl phthalate (DIDP) or diisononyl phthalate (DINP), and has a probability of being used instead of DINP depending on performance required in fields using the DPHP. Therefore, the DPHP may be suitable as a material replacing phthalate products such as DEHP, DINP, and the like when it is possible to improve a few physical properties such as plasticizing efficiency and the like.

Also, according to one exemplary embodiment of the present invention, the plasticizer composition may further include a citrate-based material. In this case, the citrate-based material may be one single compound or a mixture of two or more types selected from hybrid alkyl-substituted citrates having 4 to 9 carbon atoms and non-hybrid alkyl-substituted citrates having 4 to 9 carbon atoms, and the alkyl may be linear or branched.

The hybrid alkyl-substituted citrates having 4 to 9 carbon atoms may, for example, include a citrate having combined substituents of alkyl groups having 4 and 8 carbon atoms, such as 1,2-dibutyl-3-(2-ethylhexyl)-2-hydroxypropane-1,2, 3-tricarboxylate, 1,3-dibutyl-2-(2-ethylhexyl)-2-hydroxypropane-1,2,3-tricarboxylate, 1-butyl-2,3-bis(2-ethylhexyl)-2-hydroxypropane-1,2,3-tricarboxylate, or 2-butyl-1,3-bis(2-ethylhexyl)-2-hydroxypropane-1,2,3-tricarboxylate; and a citrate having combined substituents of alkyl groups having 5 and 7 carbon atoms, such as 1,2-dipentyl-3-heptyl-2-hydroxypropane-1,2,3-tricarboxylate, 1,3-dipentyl-2-heptyl-2-hydroxypropane-1,2,3-tricarboxylate, 1-pentyl-2,3-diheptyl-2-hydroxypropane-1,2,3-tricarboxylate, or 2-butyl-1,3-diheptyl-2-hydroxypropane-1,2,3-tricarboxylate, and the like. In addition, a citrate having combined substituents of two alkyl groups whose carbon atoms are different from each other and are selected from 4 to 9 may be used. In this case, the citrate may be one single compound or a mixture of two or more types, and the alkyl group may be linear or branched.

In the non-hybrid alkyl-substituted citrate having 4 to 9 carbon atoms, the alkyl group having 4 to 9 carbon atoms may be linear or branched. For example, tributyl citrate (TBC), tripentyl citrate (TPC), trihexyl citrate (THC), triheptyl citrate (THC), trioctyl citrate (TOC), trinonyl citrate (TNC), and the like may be used as the non-hybrid alkyl-substituted citrate. The non-hybrid alkyl-substituted citrate may be one single compound or a mixture of two or more types selected from these citrates, and the butyl group and the nonyl group may include all types of structural isomers. For example, the butyl group may include an isobutyl group, and the octyl group may include 2-ethylhexyl group.

The tributyl citrate and/or tri(2-ethylhexyl) citrate may be used at a lower frequency as the non-hybrid alkyl-substituted citrate, but the present invention is not limited thereto. For example, triisobutyl citrate may be preferably used.

Also, the hybrid alkyl-substituted citrate is a composition formed through a trans-esterification reaction of tri(2-ethylhexyl) citrate with butanol or isobutanol. In this case, mixtures including two or more citrates may be used. Specifically, the mixtures may be divided according to the number of alkyl groups with which three ester groups present in the citrate are substituted, and may include compositions including a total of 6 citrates, that is, a citrate in which all ester groups are substituted with three alkyl group, citrates which the ester groups are substituted with two of the three alkyl groups, citrates in which the ester group is substituted with one of the three alkyl groups, and a citrate in which no ester group is substituted as a reactant.

Meanwhile, the hybrid or non-hybrid alkyl-substituted citrate compound such as trialkyl citrate, di-n-alkyl-m-alkyl citrate, and the like may be used, and an acetyl citrate compound in which a hydrogen atom of the remaining hydroxyl group is substituted with an acetyl group in addition to the three ester groups may also be used as the citrate-based material.

Here, the di(2-propylheptyl) phthalate and the citrate-based material in the plasticizer composition may be included at a weight ratio of 99:1 to 1:99. For example, the di(2-propylheptyl) phthalate and the citrate-based material may be included at a weight ratio of 99:1 to 20:80, 99:1 to 40:60, 99:1 to 50:50, or 99:1 to 60:40, and may preferably be included at a weight ratio of 95:5 to 50:50, or 90:10 to 60:40.

The plasticizer composition includes the di(2-propylheptyl) phthalate and the citrate-based material, and may also further include an epoxidized ester.

The plasticizer composition in which the di(2-propylheptyl) phthalate and the citrate-based material are mixed may have relatively poor heat-resistant characteristics with respect to various physical properties. Such poor heat-resistant characteristics may be improved by adding the epoxidized ester.

The epoxidized ester may be preferably added at a content of 1 to 50 parts by weight based on 100 parts by weight of the sum of weights of the phthalate-based material and the citrate-based material. When the epoxidized ester is added at a content of greater than 50 parts by weight, mechanical properties may be relatively degraded. Therefore, the epoxidized ester to be additionally added may be preferably added at an amount relatively lower than a weight of a conventional two-component plasticizer composition.

The epoxidized ester may be an epoxidized oil, an epoxidized alkyl monoester, or a mixture thereof, and the epoxidized oil may be epoxidized soybean oil, epoxidized castor oil, epoxidized linseed oil, epoxidized palm oil, or a mixture thereof. Preferably, epoxidized soybean oil (ESO) or epoxidized linseed oil (ELO) may be used, but the present invention is not limited thereto. Also, the epoxidized alkyl monoester may be an epoxidized alkyl stearate, an epoxidized alkyl oleate, an epoxidized alkyl linoleate, and a mixture thereof, all of which contain a linear or branched alkyl group having 1 to 10 carbon atoms (a branched alkyl group having three or more carbon atoms) as an alkyl group.

In the present invention, a method for preparing the plasticizer composition may be carried out using a blending method. One example of the blending method is as follows.

The plasticizer composition may be prepared by preparing di(2-propylheptyl) phthalate and a citrate-based material and blending the di(2-propylheptyl) phthalate and the citrate-based material at a weight ratio of 1:99 to 99:1, wherein the citrate-based material is a single compound or a mixture.

When the citrate-based material is a single compound, the citrate-based material may be prepared through a direct esterification reaction in which citric acid reacts with one alcohol selected from primary alcohols having 4 to 9 carbon atoms.

The direct esterification reaction may include adding citric acid to an alcohol, adding a catalyst thereto, and allowing the citric acid to react with the alcohol under a nitrogen atmosphere; removing an unreacted alcohol and neutralizing an unreacted acid; and dehydrating and filtering the resulting reaction solution through distillation under reduced pressure.

Also, the alcohol used in the blending method may be used at a content of 150 to 1,000 mol %, 200 to 800 mol %, 300 to 6,000 mol %, 300 to 500 mol %, or 300 to 400 mol % based on 100 mol % of the citric acid.

Meanwhile, the catalyst for the direct esterification reaction used in the blending method may, for example, include one or more selected from acid catalysts such as sulfuric acid, hydrochloric acid, phosphoric acid, nitric acid, p-toluenesulfonic acid, methanesulfuric acid, ethanesulfuric acid, propanesulfuric acid, butanesulfuric acid, alkyl sulfuric acid, and the like, metal salts such as aluminum lactate, lithium fluoride, potassium chloride, cesium chloride, calcium chloride, iron chloride, aluminum phosphate, etc., metal oxides such as heteropoly acid, and the like, organic metals such as natural/synthetic zeolite, cation and anion exchange resins, tetra-alkyl titanate, and polymers thereof. As one specific example, tetra-alkyl titanate may be used as the catalyst.

An amount of the catalyst used may vary depending on the type of catalyst. For example, a homogeneous catalyst may be used in a content range of 0.01 to 5% by weight, 0.01 to 3% by weight, 1 to 5% by weight, or 2 to 4% by weight, based on a total of 100% by weight of the reactants, and a heterogeneous catalyst may be used in a content range of 5 to 200% by weight, 5 to 100% by weight, 20 to 200% by weight, or 20 to 150% by weight, based on a total of 100% by weight of the reactants.

In this case, a reaction temperature may be in a range of 180 to 280° C., 200 to 250° C., or 210 to 230° C.

When the citrate-based material is a mixture, a terephthalate compound may be prepared through a direct esterification reaction in which citric acid reacts with one alcohol selected from primary alcohols having 4 to 9 carbon atoms; or a trans-esterification reaction in which one alcohol selected from primary alcohols having 4 to 9 carbon atoms reacts with one citrate selected from non-hybrid alkyl-substituted citrates having 4 to 9 carbon atoms.

The "trans-esterification reaction" used in the present invention refers to a reaction in which an alcohol reacts with an ester, as shown in the following Scheme 1, so that R" of the ester can be interchanged with R' of the alcohol, as shown in the following Scheme 1.

[Scheme 1]

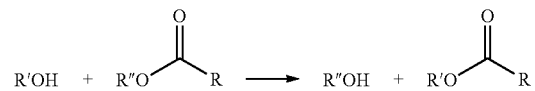

According to one exemplary embodiment of the present invention, when the trans-esterification reaction is carried out, three ester compositions may be formed according to three cases, that is, when an alkoxide of the alcohol attacks carbons of two ester groups (RCOOR") present in an ester-based compound; when the alkoxide of the alcohol attacks carbons of one ester group (RCOOR") present in the ester-based compound; and when a reaction is not carried out.

Also, the trans-esterification reaction has an advantage in that a wastewater problem is not caused in comparison to an acid-alcohol esterification reaction, and problems caused by the use of an acid catalyst may be solved because such a reaction may be carried out in the absence of a catalyst.

For example, the tri(2-ethylhexyl) citrate and the butyl or isobutyl alcohol may be subjected to the trans-esterification reaction to form a mixture of citrates from the tri(2-ethylhexyl) citrate having three (2-ethylhexyl) groups substituted therein: two compounds in which one (2-ethylhexyl) group is substituted with a butyl group, two compounds in which two (2-ethylhexyl) groups are substituted with butyl groups, tributyl citrate in which three (2-ethylhexyl) groups are substituted with butyl groups, and unreacted tri(2-ethylhexyl) citrate.

In the mixture, the six citrates may be divided into three groups: a citrate group in which (2-ethylhexyl) groups are substituted with two butyl groups, a citrate group in which a (2-ethylhexyl) group is substituted with one butyl group, and a citrate group in which no (2-ethylhexyl) group is substituted with a butyl group. Composition ratios of the three groups may be properly adjusted according to the content of alcohol added. When the composition ratios are properly adjusted, a citrate-based material having high processing efficiency and excellent processability and absorption rate may be obtained.

The composition ratios of the three groups may be in a range of 0 to 15% by weight, 5 to 40% by weight, 20 to 70% by weight, and 30 to 80% by weight for the material having three butyl groups substituted therein, the material having two butyl groups substituted therein, the material having one butyl group substituted therein, and the material having no butyl group substituted therein, respectively. As such, when the mixture is prepared through the trans-esterification reaction, a composition ratio of the mixture may be controlled depending on an amount of alcohol added.

The amount of alcohol added may be in a range of 0.1 to 89.9 parts by weight, particularly in a range of 3 to 50 parts by weight, and more particularly in a range of 5 to 40 parts by weight, based on 100 parts by weight of the citrate-based material.

Because a mole fraction of the citrates participating in the trans-esterification reaction increases as the amount of alcohol added increases in the case of the citrate-based material, a content of the compounds having many butyl groups substituted therein as the products in the mixture may tend to increase, and a content of the citrates remaining unreacted may decrease accordingly.

However, a certain composition ratio in the mixture of the six citrates is not limited. For example, the composition ratio may be changed by additionally adding one of the six terephthalates.

According to one exemplary embodiment of the present invention, the trans-esterification reaction is preferably performed at a reaction temperature of 120 to 190° C., preferably at a reaction temperature of 135 to 180° C., and more preferably at a reaction temperature of 141 to 179° C. for 10 minutes to 10 hours, preferably for 30 minutes to 8 hours, and more preferably for 1 to 6 hours. Within the temperature and time ranges, a citrate mixture having a desired composition ratio may be effectively obtained. In this case, the reaction time may be calculated from a point of time to reach the reaction temperature after increasing the temperature for the reactants.

The trans-esterification reaction may be carried out in the presence of an acid catalyst or a metal catalyst, which provides an effect of reducing the reaction time.

The acid catalyst may, for example, be sulfuric acid, methanesulfonic acid, or p-toluenesulfonic acid, and the metal catalyst may, for example, be an organic metal catalyst, a metal oxide catalyst, a metal salt catalyst, or a metal itself.

The metal component may, for example, be one selected from the group consisting of tin, titanium, and zirconium, or a mixture of two or more types thereof.

Also, the method may further include removing an unreacted alcohol and a reaction by-product, for example, an ester-based compound represented by Formula 3, through distillation after the trans-esterification reaction.

The distillation may, for example, be a two-stage distillation using a difference in boiling points between the alcohol and the reaction by-product.

By way of another example, the distillation may be a mixed distillation. In this case, the distillation has an effect of obtaining an ester-based plasticizer composition with a desired composition ratio in a relatively stable manner. The mixed distillation refers to process in which butanol and a reaction by-product are simultaneously distilled.

The method may further include adding the aforementioned epoxidized ester when necessary after the citrate-based material is blended with the di(2-propylheptyl) phthalate. When the epoxidized ester is added, heat resistance of the plasticizer composition used may be further enhanced.

The plasticizer composition may further include an additive, and the additive may include one or more selected from the group consisting of a filler, a stabilizer, a processing aid, a lubricant, a dispersant, a foaming agent, a viscosity depressant, and titanium dioxide. The additive may be added to the plasticizer composition, and may also be added to the plasticizer composition further including the epoxidized ester. Also, the additive may be added to the resin composition before the plasticizer composition is used after being mixed with the resin. That is, when used with the resin, the additive may be added at any stage before products are manufactured using the resin composition. In this case, the additive may be preferably added by suitably adjusting a content of the additive to give each function.

The plasticizer composition thus prepared may be included in a content range of 5 to 150 parts by weight, 40 to 100 parts by weight, or 40 to 50 parts by weight based on 100 parts by weight of the resin selected from ethylene vinyl acetate, polyethylene, polypropylene, polyvinyl chloride, polystyrene, polyurethane, and a thermoplastic elastomer, and thus a resin composition effective for all of a compound formulation, a sheet formulation, and a plastisol formulation may be provided.

For example, the plasticizer composition may be applied to the manufacture of an electric wire, a flooring material, an automotive interior material, a film, a sheet, wallpaper, or a tube.

The invention claimed is:

1. A plasticizer composition comprising di(2-propylheptyl) phthalate; and a citrate-based material,
   wherein the di(2-propylheptyl) phthalate and the citrate-based material are included at a weight ratio of 95:5 to 50:50, and
   wherein the citrate-based material is one single compound or a mixture of two or more types selected from hybrid alkyl-substituted citrates having 4 to 9 carbon atoms and non-hybrid alkyl-substituted citrates having 4 to 5 carbon atoms, and the alkyl is linear or branched.

2. The plasticizer composition of claim 1, wherein the di(2-propylheptyl) phthalate and the citrate-based material are included at a weight ratio of 95:5 to 60:40.

3. The plasticizer composition of claim 1, wherein the citrate-based material is one single compound or a mixture of two or more types selected from hybrid alkyl-substituted citrates having 4 to 9 carbon atoms, and the alkyl is linear or branched.

4. The plasticizer composition of claim 1, wherein the citrate-based material is one single compound or a mixture of two or more types selected from non-hybrid alkyl-substituted citrates having 4 to 9 carbon atoms, and the alkyl is linear or branched.

5. The plasticizer composition of claim 1, wherein the plasticizer composition further comprises an additive, and the additive comprises one or more selected from the group consisting of a filler, a stabilizer, a processing aid, a lubricant, a dispersant, a foaming agent, a viscosity depressant, and titanium dioxide.

6. The plasticizer composition of claim 1, wherein the plasticizer composition further comprises an epoxidized ester.

7. The plasticizer composition of claim 6, wherein the epoxidized ester is added at a content of 1 to 50 parts by weight based on 100 parts by weight of the sum of weights of the phthalate-based material and the citrate-based material.

8. The plasticizer composition of claim 6, wherein the epoxidized ester is an epoxidized oil, an epoxidized alkyl monoester, or a mixture thereof, the epoxidized oil comprises one or more selected from the group consisting of epoxidized soybean oil, epoxidized castor oil, epoxidized linseed oil, epoxidized palm oil, and epoxidized tall oil, and the epoxidized alkyl monoester has 1 to 10 carbon atoms.

9. The plasticizer composition of claim 6, wherein the plasticizer composition further comprises an additive, and the additive comprises one or more selected from the group consisting of a filler, a stabilizer, a processing aid, a lubricant, a dispersant, a foaming agent, a viscosity depressant, and titanium dioxide.

10. A method for preparing a plasticizer composition, comprising:

preparing di(2-propylheptyl) phthalate and a citrate-based material; and blending the di(2-propylheptyl) phthalate and the citrate-based material at a weight ratio of 95:5 to 50:50 to obtain a plasticizer composition, wherein the citrate-based material is one single compound or a mixture of two or more types selected from hybrid alkyl-substituted citrates having 4 to 9 carbon atoms and non-hybrid alkyl-substituted citrates having 4 to 9 carbon atoms, and the alkyl is linear or branched.

11. The method of claim 10, wherein, when the citrate-based material is a single compound, the citrate-based material is prepared through a direct esterification reaction in which citric acid reacts with one alcohol selected from primary alcohols having 4 to 9 carbon atoms.

12. The method of claim 10, wherein, when the citrate-based material is a mixture, a terephthalate compound is prepared through a direct esterification reaction in which citric acid reacts with one alcohol selected from primary alcohols having 4 to 9 carbon atoms; or a trans-esterification reaction in which one alcohol selected from primary alcohols having 4 to 9 carbon atoms reacts with one citrate selected from non-hybrid alkyl-substituted citrates having 4 to 9 carbon atoms.

13. The method of claim 10, further comprising:

adding an epoxidized ester after the blending.

14. A resin composition comprising:

100 parts by weight of a resin; and 5 to 150 parts by weight of the plasticizer composition defined in claim 1.

15. The resin composition of claim 14, wherein the resin comprises one or more selected from the group consisting of ethylene vinyl acetate, polyethylene, polypropylene, polyketone, polyvinyl chloride, polystyrene, polyurethane, and a thermoplastic elastomer.

16. The resin composition of claim 14, wherein the resin composition further comprises an additive, and the additive comprises one or more selected from the group consisting of a filler, a stabilizer, a processing aid, a lubricant, a dispersant, a foaming agent, a viscosity depressant, and titanium dioxide.

17. The resin composition of claim 14, wherein the resin composition comprises one or more materials for products selected from the group consisting of an electric wire, a flooring material, an automotive interior material, a film, a sheet, wallpaper, and a tube.

* * * * *